United States Patent
Mutter

[11] 3,999,864
[45] Dec. 28, 1976

[54] GLOSS MEASURING INSTRUMENT

[75] Inventor: Walter E. Mutter, Poughkeepsie, N.Y.

[73] Assignee: International Business Machines Corporation, Armonk, N.Y.

[22] Filed: Nov. 17, 1975

[21] Appl. No.: 632,615

[52] U.S. Cl. .............................. 356/212; 250/227; 350/96 B; 356/209

[51] Int. Cl.² ....................................... G01N 21/48

[58] Field of Search .......... 250/226, 227; 350/96 B; 356/209–212, 186, 188, 189

[56] References Cited

UNITED STATES PATENTS

| | | | |
|---|---|---|---|
| 3,549,264 | 12/1970 | Christie | 250/227 X |
| 3,751,643 | 8/1973 | Dill et al. | 235/151.32 |

OTHER PUBLICATIONS

American Instrument Company, Bulletin 2115, May 1943, pp. 1–4.
Hunterlab Model D–16 Multipurpose Glossmeter, Oct. 1961, pp. 1–4.

Primary Examiner—John K. Corbin
Assistant Examiner—F. L. Evans
Attorney, Agent, or Firm—Douglas R. McKechnie

[57] ABSTRACT

An instrument for measuring the gloss of test samples at different predetermined angles of incidence, includes a glossimeter head operative to receive polychromatic light and direct it along plural beams at different angles of incidence towards an area on the surface to be analyzed. A plurality of light receptors are arranged to receive specular light reflected from the surface at different angles of reflection corresponding to the angles of incidence. The receptors include plural filters each one operative to pass light at a different wavelength than the others. The light collected by the receptors is passed through a monochromator to a light detector whereby the light directed at the different angles of incidence and reflections corresponds to different wavelengths. Fiber optic light pipes may be used to transmit light through the instrument. A plug type coupling may be used to convert a general purpose spectrophotometer to the purpose of measuring gloss.

10 Claims, 7 Drawing Figures

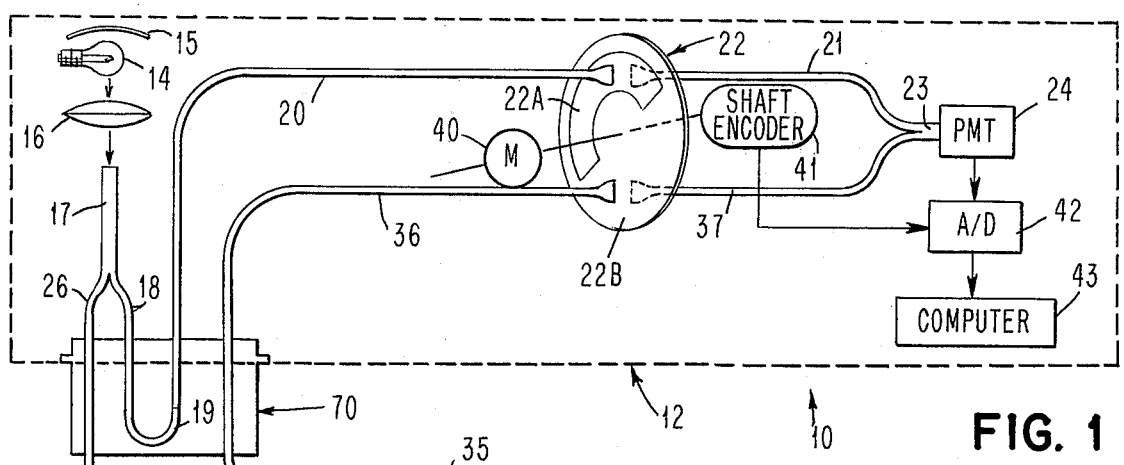
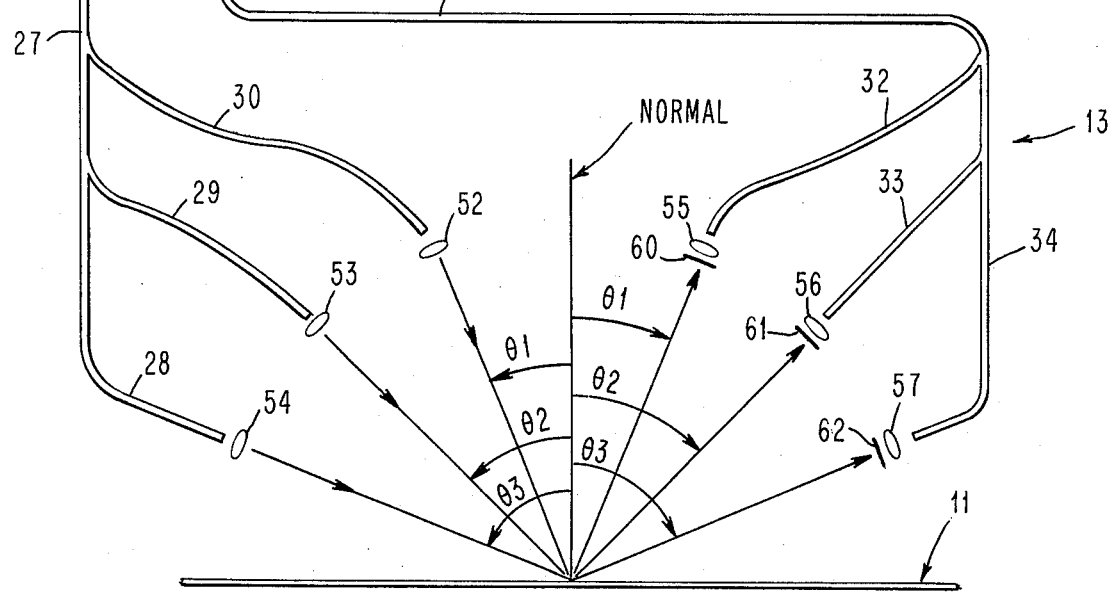
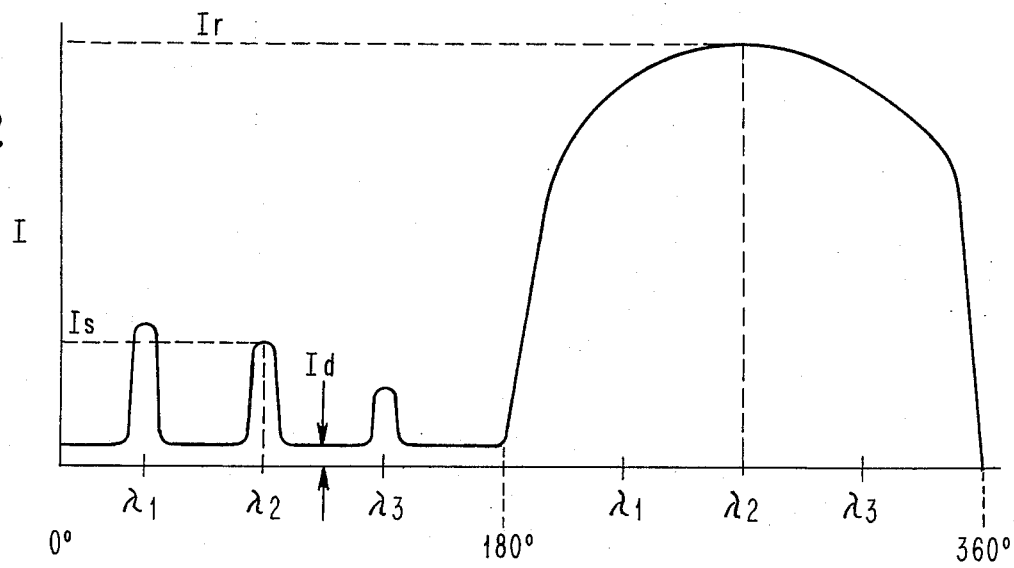
FIG. 1
FIG. 2

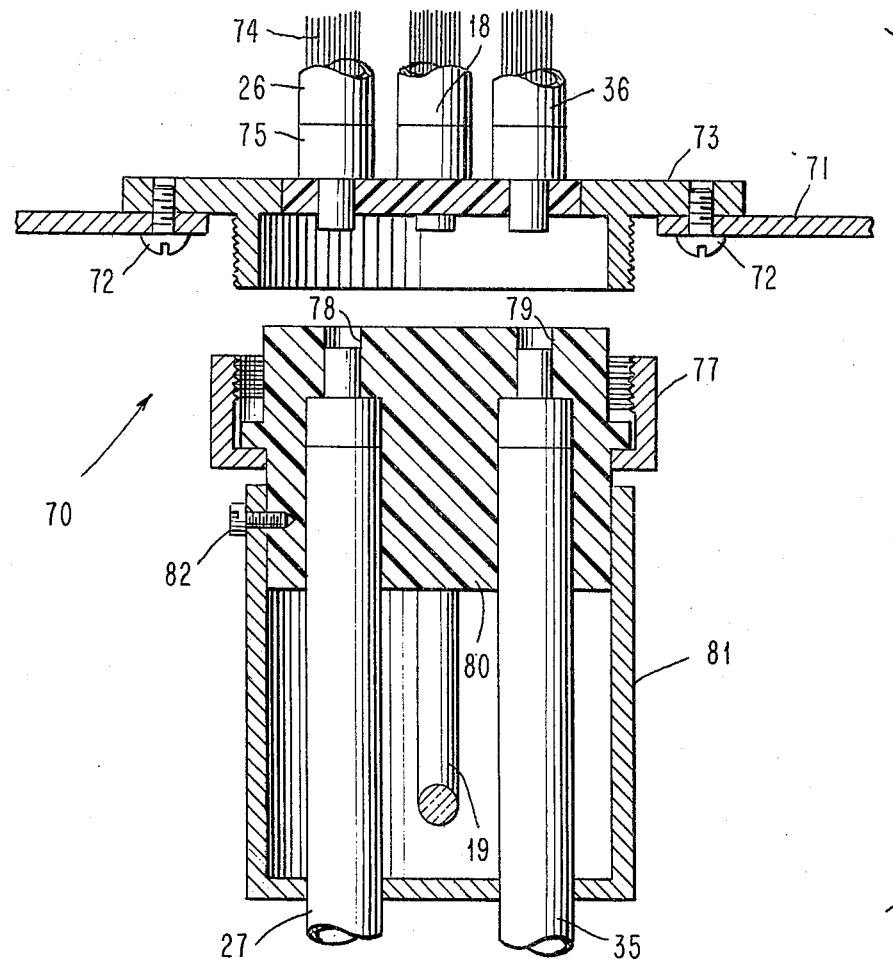
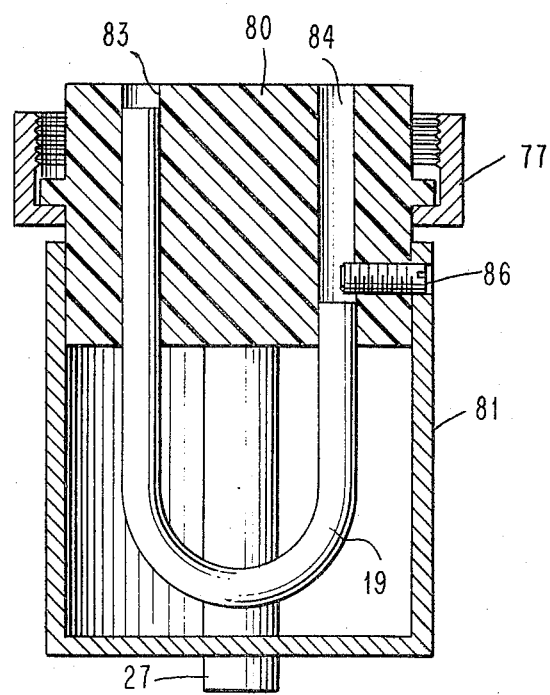

GLOSS MEASURING INSTRUMENT

FIELD OF THE INVENTION

This invention relates to improvements in instruments for measuring gloss.

PRIOR ART

Gloss or specular reflection represents the degree to which a surface possesses the light reflecting property of a perfect mirror. In many industries, such as the paint industry or paper industry, it is customary to measure the gloss characteristics of the associated products. The gloss of any surface is a function of the angle of incidence. By convention or standardization within an industry, it has been customary to measure gloss at several different pre-specified angles of incidence generally ranging from 10° to 80°.

Various instruments are available to measure gloss. Some do so at a single fixed angle, some do so at various fixed angles and some involve a variable angle of incidence spanning the entire range. The present invention is concerned with measuring gloss at different fixed angles.

In the prior art, instruments for measurng gloss at fixed angles generally employ some form of an illumination system that directs light onto a surface at different angles and light receptors and collectors are mounted at different angles, the various receptors transmitting the light to different photoelectric devices to provide different outputs for the various different angles of incidence. In such instruments, the different detectors create in effect different channels that have to be scanned or measured in order to detect the desired output. In addition, to achieve a high degree of accuracy, the various photodetectors have to be calibrated or matched. In contrast, the subject invention involves the use of a single detector and a plurality of receptors arranged at different angles to provide gloss readings at these different angles.

Also known in the prior art are various forms of spectrophotometers designed to measure the reflectance properties of different surfaces for various reasons. One particular type of spectrophotometer is disclosed in U.S. Pat. No. 3,751,643 - Dill et al, assigned to the Assignee of the present application. Such instrument includes a rotatable variable interference filter that acts as a monochromator to convert polychromatic light into a narrow band of variable monochromatic light. The filter is mounted for rotation and the instrument includes a shaft encoder that provides signals that are a function of the angular position of the shaft from a reference point. Consequently, the wavelength of the monochromatic light being transmitted by the filter at any particular instance is a function of its angular displacement. An optical system is provided that includes both a reference path and a sample path for directing light from a wide band energy source along both paths towards a photodetector such as a photomultiplier tube. In one path, the light is reflected off of the sample and in the other path light is transmitted directly from the light source towards the photodetector. The monochromator is disposed in both light path means so that one transmits light while the other is blocked, and vice versa. The particular instrument there disclosed was primarily designed to be used for measuring the thickness of thin films deposited on semi-conductor substrates but, as pointed out, the instrument could be used to examine the reflectance characteristics of other surfaces.

It is possible to construct a spectrophotometer of the type disclosed in the above mentioned patent to perform different functions on different test samples, where the various test samples and specific tests require different forms of heads or holders for illuminating the test sample and collecting light reflected therefrom. It is thus possible to construct such instruments wherein the light paths include fiber optic bundles that can, through conventional coupling, or connectors, have a disconnectable connection with the instrument whereby the basic functions of the instrument can be changed by using different types of attachments or heads. The subject invention is designed as an attachment for use with spectrophotometers of the type disclosed in the above mentioned patent.

SUMMARY OF THE INVENTION

One of the objects of the invention is to provide improved apparatus for measuring the gloss characteristics of a surface at different angles of incidence.

Another object of the invention is to provide a glossimeter head for attachment to a spectrophotometer for the purpose of enabling the spectrophotometer to measure the gloss characteristics of a surface.

Still another object of the invention is to provide a glossimeter head in which the test surface is illuminated by beams directed at different angles of incidence and in which receptors are aligned with such beams at the different angles of reflection corresponding to the angles of incidence, and wherein filters that transmit light of different wavelengths are respectively used to identify the various angles of incidence.

A further object of the invention is to provide a gloss measuring instrument having a single photodetector that is actuated by light transmitted along paths arranged at different angles of incidence relative to a test surface.

Briefly stated, the invention comprises a sample illumination path in which plural beams of light are directed at the test surface at different angles of incidence. Light receptors are mounted in alignment with the respective angles of incidence at different angles of reflection corresponding thereto. Plural filters for transmitting light at different wavelengths are disposed in the different beams of light to identify the respective angles of incidence according to the wavelengths transmitted by the filters. The light is transmitted along fiber optic bundles towards a photodetector and a monochromator cooperates with such bundles so that only monochromatic light of variable wavelength reaches the photodetector. This thus provides output signals at different wavelengths that are a function of the angles of incidence.

Other objects and advantages of the invention will be apparent from the following more detailed description of a preferred embodiment of the invention, taken in connection with the accompanying drawings wherein:

FIG. 1 is a schematic diagram of an instrument embodying the invention;

FIG. 2 is an exemplary graph of the photodetector output of the instrument of FIG. 1, for illustrating operation of the invention;

FIG. 4 is a cross-sectional view through the coupling mechanism;

FIG. 5 is a cross-sectional view through the plug assembly showing the portion of the reference path therein;

DETAILED DESCRIPTION

Figure 3:
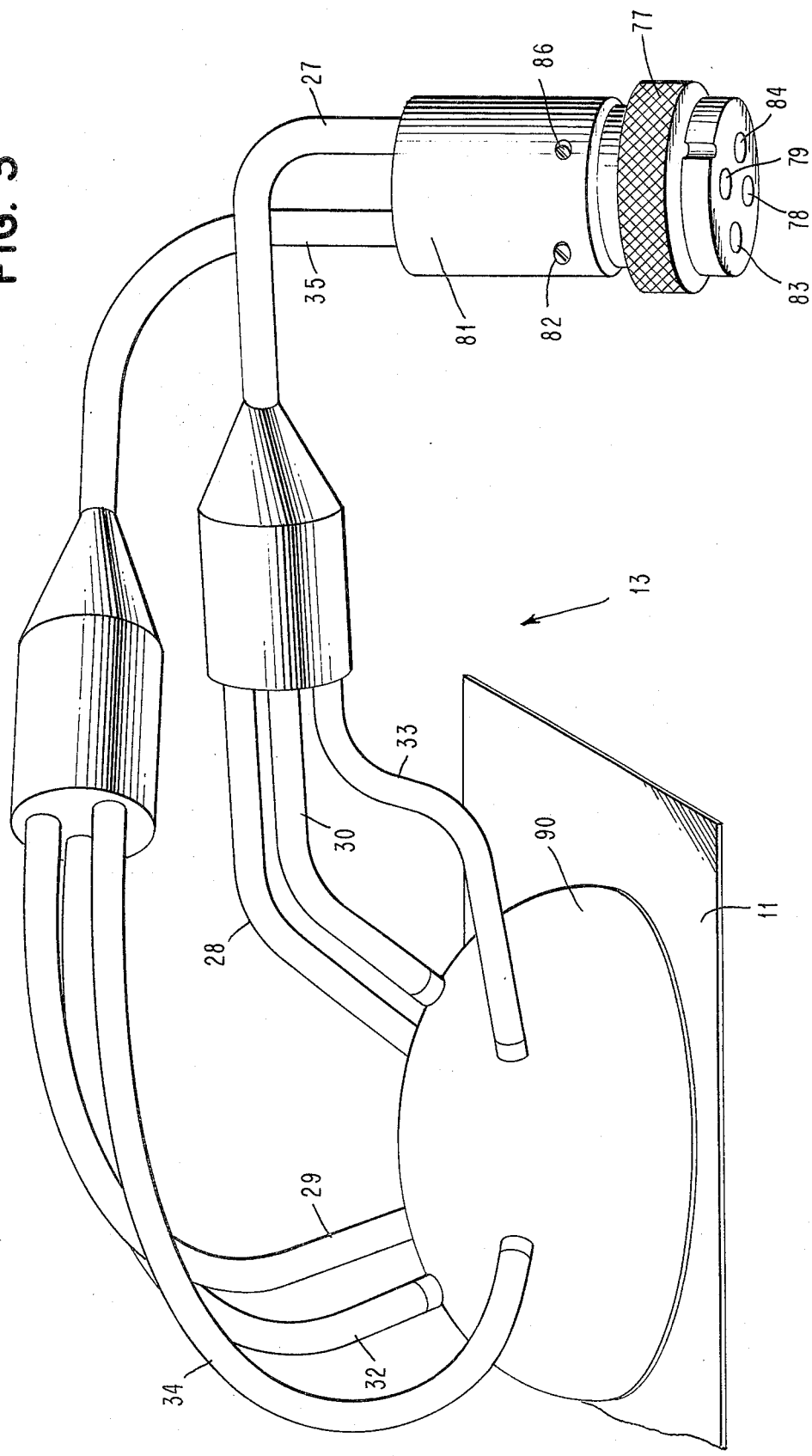
FIG. 3 is a perspective view of a glossimeter head attachment for a spectrophotometer, embodying the invention.

Referring now to the drawing, and first to FIG. 1, there is illustrated a spectrophotometer 10 adapted for measuring the gloss of a flat test sample 11. The test sample may be, for example, a piece of paper or plastic, or a flat surface that has been painted. Spectrophotometer 10 generally includes an instrument section 12 and a glossimeter attachment 13 including a sample illumination and light collection system described in detail below.

Spectrophotometer 10 includes a wide band polychromatic light source 14 disposed in front of a reflecting mirror 15 that directs light received thereby towards a lens 16. Lens 16 receives light from lamp 14 both directly and indirectly from reflector 15 and concentrates such light on the light inlet or entrance of a fiber optic bundle 17. This bundle forms part of a light pipe system that includes a reference path and a sample or test path. Fiber optic bundle 17, along with all of the other fiber optic bundles described below, is composed or randomly oriented strands of fiber optics.

The other end of bundle 17 is bifurcated. One end 18 forms part of the reference path whereby light transmitted along this path traverses or passes through bundle 18, a light pipe 19 and a fiber optic bundle 20. The end of bundle 20 is aligned with but spaced from the end of a fiber optic bundle 21. Between the adjacent ends of bundles 20 and 21 is a rotary monochromator 22 comprised of a variable wedge type intereference filter 22a that extends around 180° of the monochromator and an opaque portion 22b that extends for the other 180°. As the monochromator 22 rotates, light is transmitted through the length of the reference path only when filter 22a lies between the adjacent ends of bundles 20 and 21. The ends of these bundles may be flattened as shown in FIG. 1 or they may cooperate with a mask (not shown) having a slit therein whereby the width of the ends or of the slit establishes the bandwidth of the monochromatic light that is passed by filter 22a. Filter 22a is uniformly graduated from one end to the other to pass light spanning the visible portion of the light spectrum. Bundle 21 forms part of a larger bundle 23 as connected to a photodetector such as a photomultiplier tube (PMT) 24 that provides an output signal proportional to the intensity of light received thereby.

The aforementioned sample path includes an end 26 of bundle 17 aligned with fiber optic bundle 27 the lower portion of which, as viewed in FIG. 1, is split into three separate ends 28, 29 and 30 each of which transmits an approximately equal amount of light. These ends are oriented, as described in detail below, to illuminate test sample 11. Light reflected from the test sample is collected by receptors or fiber optic bundles 32, 33 and 34 which are merged into a single bundle 35. The end of bundle 35 is aligned with the entrance of a bundle 36 in the instrument section 12 which transmits light to one side of monochromator 22. Disposed on the other side of monochromator 22 is another bundle 37 the end of which is aligned with the end of bundle 36 to receive light transmitted through filter 22a when it lies between the adjacent ends. Bundle 37 is merged into bundle 33 for transmitting light therealong to PMT 24.

Monochromator 22 is rotated by a motor 40, and a shaft encoder 41 rotates therewith to provide a series of signals indicative of the angular position of monochromator 22. These signals are at regularly spaced angular positions of rotation whereby the nominal wavelength of the monochromatic light being transmitted by filter 22 is a function of the angular displacement. The signals are fed to a computer 43 which forms part of the instrument section 12. Also fed to computer 43 are signals from an analog-to-digital (A/D) converter 42 connected to receive the output of PMT 24 and provide digital values indicative of the output signal. During one revolution of monochromator 22, the output of PMT 24 varies as shown, by way of example, in FIG. 2, described below.

Mounted in front of the ends of fiber optic bundles 28, 29 and 30 are three lenses 54, 53, and 52 respectively designed to gather light emerging from the adjacent ends of the bundles and collimate beams thereof to a spot or area of the test sample to be analyzed. The light beams as thus formed by the bundles 28 – 30 and lenses 54 – 52 are directed at different angles of incidence $\theta 1$, $\theta 2$, and $\theta 3$ which are prefixed or predetermined and chosen in accordance with whatever standards or conventions are used for measuring the gloss of the particular sample. Disposed in front of bundles 32, 33 and 34 are three lenses 55, 56 and 57 that collect light reflected from the test sample and concentrate the beams on the adjacent entrance ends of bundles 32–34. Disposed in front of these lenses are three filters 60, 61 and 62 designed respectively to pass narrow bandwidth beams of monochromatic light at nominal wavelengths of $\lambda_1$, $\lambda_2$ and $\lambda_3$ respectively. The axis of bundles 32 – 34 and of lenses 55 – 57 are oriented to receive primarily specular light reflected from sample 11 at angles of reflections $\theta 1$, $\theta 2$ and $\theta 3$ aligned with and corresponding to the angles of incidence described above. It is to be appreciated that FIG. 1 is a schematic representation of the system and the specific construction of attachment is described below.

It is to be also appreciated that instrument section 12 of spectrophotometer 10 is of a general purpose nature and can be used with different attachments for different purposes other than measuring gloss. For example, the system may be constructed as described in the aforementioned U.S. Pat. No. 3,751,643, for measuring the thickness of thin films. It could also be used to measure the reflectance of colored surfaces for analyzing the color thereof. It could also be used as a double beam spectrophotometer wherein the reference path, through a suitable sample holder, would allow the elimination of a standard in addition to a sample.

To achieve such versatility, spectrophotometer 10 includes a coupling or connector 70 the details of which are shown primarily in FIG. 4. In general, the connector is similar to a conventional type used commonly in connecting electric cables having multiple conductors except that fiber optic bundles are substituted for the conductors. More specifically, and with reference to FIG. 4, instrument portion 12 of spectrophotometer 10 includes a panel 71 on which is mounted by screws 72 a member 73 the center portion of which receives the reduced end portions of fiber optic bundles 26, 18, 20 and 36. The fiber optic bundles are of conventional construction and, as shown for bundle 26 in FIG. 4, include an inner core 74 of randomly oriented fiber optics surrounded throughout the medial portion of the bundle by an outer protective sheath and having, at the ends, metal ferrules 75 having tips of reduced diameter, the ends of the fiber optic strand 74 extending through the tips and being exposed to receive or emit light. The tips of the respective ferrules stick through member 73 and project slightly outwardly thereof and are surrounded by a threaded annular collar 76.

The other half of connector 70 comprises a knurled internally threaded ring rotatable 77 adapted to be engaged with collar 76 for connecting the mating parts of the connector assembly together. A cylindrical block 80 receives the end portions of fiber optic bundles 27 and 35 and includes recesses 78 and 79 adapted to receive the tips of bundles 26 and 36 when connector 70 is coupled together. A Cap 81 is connected by a screw 82 to block 80.

The reference path through connector 70 is shown in FIG. 5 and comprises a light pipe 19 which fits into a bore having recesses 83 and 84 adapted to mate with the respective ends of fiber optic bundles 18 and 20. This light pipe may be in the form of a glass rod coated so as to have a high degree of internal reflection. Alternatively, it may also be comprised of fiber optic strands. One end of light pipe 19 terminates within a chamber the outer portion of which forms recess 84 and this chamber intersects with a threaded bore which receives a set screw 86. The purpose of the set screw is to provide means for attenuating the amount of light passing along the reference path and this amount of light would be initially calibrated so that the peak current produced by PMT 24 along the reference path is approximately equal to the peak current produced by light travelling through the sample path when calibrated on a surface having 100% gloss or specular reflection characteristics. Alternatively, the amount of light transmitted along the respective paths can be balanced by suitable proportioning of the size of the respective bundles.

Attachment 13, shown in FIG. 3, comprises a hemispherical head 90 fabricated from metal or other rigid material. The inner surface of head 90 is hollowed out to provide a chamber 91 in which the test sample 11 is illuminated during testing. The inner surfaces of chamber 91 are coated with optical black point to suppress stray reflections. The lower edge of head 90 has a ring of sponge rubber which, when the head 90 rests upon sample 11, seals the lower edge of the head and shuts out stray light.

Figure 6:
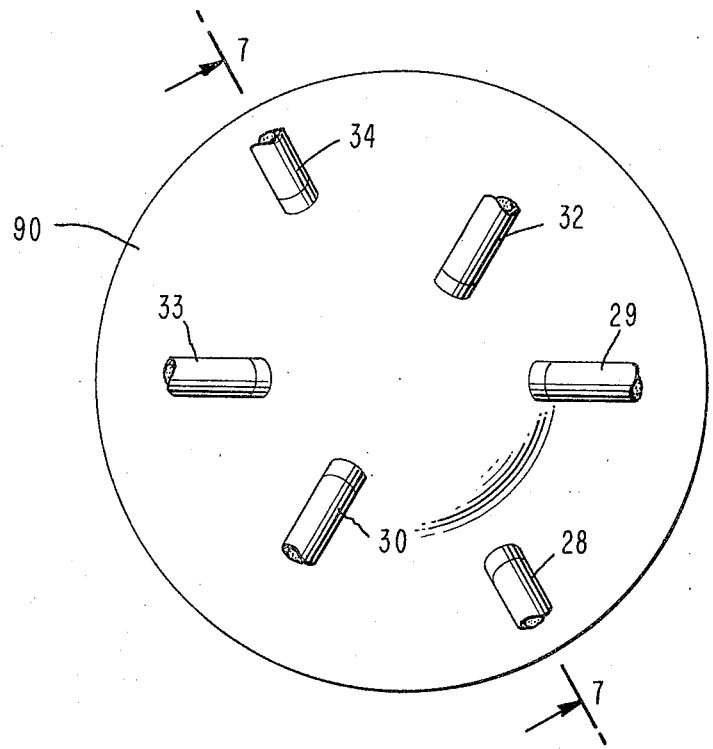
FIG. 6 is a top plan view of the sample holder head shown in FIG. 4.
Figure 7:
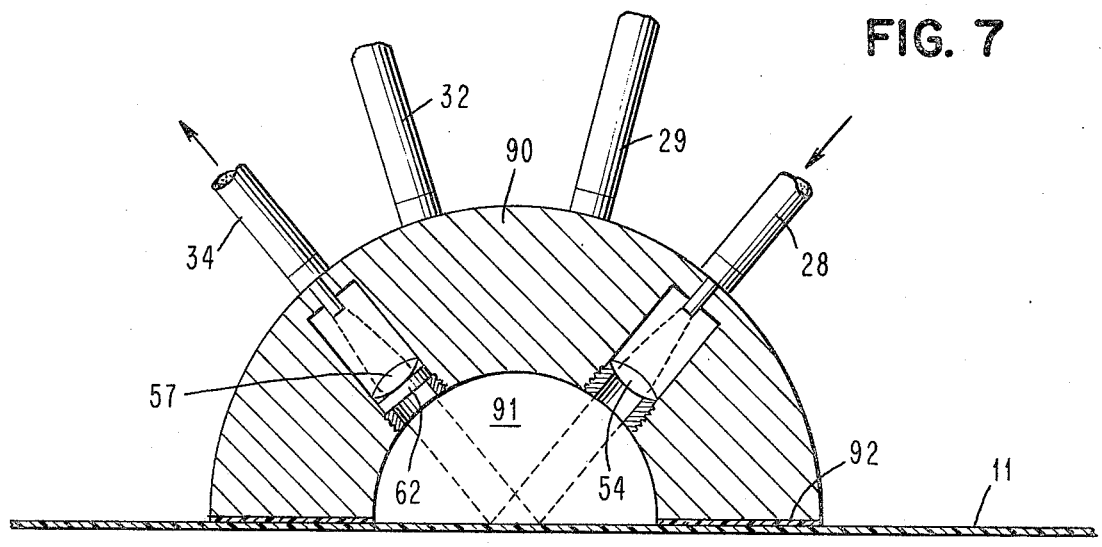
FIG. 7 is a cross-sectional view along line 7—7 of FIG. 6.

As best seen in FIG. 6 and 7, the corresponding pairs of fiber optic bundles having the same angles of incidence and reflection are located in diametrical planes on opposite side of head 90 with their axes inclined or oriented at the respective angles. These planes are perpendicular relative to the surface of 11 and are quiangularly spaced apart. Each pair is oriented in a similar manner except for the angle of incidence and of reflection so only one such pair need be described in detail. With reference to FIG. 7, fiber optic bundle 28 has one end mounted in head 90 so that light emerging therefrom is directed onto lens 54 which produces a collimated beam of light falling on a spot beneath the center of head 90. Light reflected from surface 11 first passes through filter 62 and then through lens 57 which concentrates such light upon the entrance end of fiber optic bundle 34.

OPERATION

The operation of spectrophotometer 10 for one revolution of monochromator 22 will now be described with reference to FIG. 2 which illustrates an exemplary graph of the output I of PMT 24 versus the angular displacement from a zero reference position. The zero reference position is assumed to be when the blue end of filter 22a is aligned between the adjacent ends of fiber optic bundles 36 and 37. As the filter 22a is rotated from this point, during the first 180° light will be transmitted along the sample path and during the second 180° light will be transmitted along the reference path. Let it also be assumed that filters 60 – 62 are chosen so as to have nominal wavelengths that are relatively spaced from each other to provide distinctive signals. For example, they may represent respectively blue, green and red filters having nominal wavelengths of 425, 530 and 650 millimicrons respectively. As the filter rotates through the first 180°, the output current of PMT 24 peaks at wavelengths corresponding to $\lambda 1$, $\lambda 2$ and $\lambda 3$ of the filters. During the second half of rotation, the sample path is blocked by opaque portion 22b and the reference path transmits due to filter 22a being aligned with fiber optic bundles 20 and 21. The output of PMT 24 will then vary in accordance with the respective monochromatic wavelengths contained in the polychromatic light being transmitted. As previously indicated, in the preferred embodiment of the invention shown in FIG. 1, the output of PMT 24 is converted to digital values that are fed to a computer for analysis, display or printout. It should be obvious that the analog output of PMT 24 can be fed to some form of analog recording apparatus that would produce an output curve similar to that shown in FIG. 2.

In order to measure or calculate or determine the gloss of an unknown sample, it is necessary to take measurements on both the unknown sample and on a standard of known gloss, each measurement causing the output of PMT 24 to vary similar to FIG. 2. In both instances, measurements are taken at the desired angle of incidence for which the gloss is to be determined. In the illustrated embodiment, it can be at any one of three different angles although it is to be appreciated that more or fewer angles can be provided in the instrument head. The gloss of an unknown, when measured at a given angle of incidence is calculated according to the following formula:

$$Gu = \frac{(Is)u - (Id)u}{(Is)s - (Id)s} \times \frac{(Ir)s - (Id)s}{(Ir)u - (Id)u} \times Gs$$

where
$Gu$ = percent gloss of unknown sample
$Gs$ = percent gloss of standard
$(Is)u$ = output signal from PMT 24 from unknown sample at the wavelength corresponding to the angle of incidence. This corresponds for example, to $(Is)$ shown in FIG. 2 for the unknown when measured at $\lambda 2$.
$(Is)s$ = signal from standard
$(Ir)s$ = signal in reference beam when standard is measured. By way of example, this corresponds to signal $(Ir)$ shown in FIG. 2, for the standard.

$(I_s)u$ = signal in reference beam during measurement of the unknown sample.

$(I_d)u$ = background signal in system at time unknown sample is measured, taken at a wavelength λ between λ1, λ2 and λ3.

$(I_d)s$ = background signal in system at time standard is measured.

It is to be appreciated that the purpose of the reference beam is to provide a consistent base for making the other measurements where there is a change that the intensity of light from the lamp source, or the sensitivity of the PMT may vary due to different operating conditions. If a highly stable light source is used and if measurements are made on the unknown sample and standard with as little time lapse as possible, then the reference path signals could be dropped from the above formula. In other words, under such conditions, where there is a highly stable light source and detector that reproducedly provides consistent and accurate results, then the reference path is unnecessary. However, the provision of the reference path obviates the need for any costly stabilization and power regulation and makes for easy calculations.

It should also be noted that the formula above accounts for the background signal that exists in the system when no light is incident on PMT 24. This is analogous to "dark current" measurements. Some systems include means to automatically compensate for dark current and in such systems the background signal factors would be dropped from the above equation.

Another change that can be made in the instrument section would be to substitute discrete filters (not shown) for filter 22a, the discrete filters corresponding in number and in transmission characteristics to filters 60 – 62. Thus, as 22 rotates, transmission therethrough would be limited to the desired wavelength.

It should be apparent that other changes by way of additions and omissions can be made in the details and arrangement of parts without departing from the scope of the invention as defined in the appended claims.

What is claimed is:

1. In an instrument for measuring the gloss of a test sample, the combination comprising:
 a polychromatic light source;
 a detector providing an output signal proportional to the intensity of light received thereby;
 illumination means operative to direct plural beams of illuminating light onto a surface of the test sample at different angles of incidence;
 collection means operative to collect plural beams of light reflected from said surface at different angles of reflection corresponding to said angles of incidence whereby said collection means receives primarily the specular component of such reflected light;
 plural discrete filters for transmitting monochromatic light of different wavelengths, said filters being disposed in different ones of said beams of illuminating and reflected light to provide color differentiation corresponding to the different angles of incidence and reflection;
 first light guide means for transmitting light from said source to said illumination means;
 second light guide means for transmitting light from said collection means to said detector;
 and filter means operatively connected between said light source and said detector to transmit wavelengths of monochromatic light corresponding to the different wavelengths transmitted by said discrete filters.

2. The combination of claim 1 including opaque means encompassing said illumination means and collection means and said surface and operative to prevent light from other than said illumination means from being received by said collection means.

3. The combination of claim 2 wherein said opaque means is movable relative to the test sample whereby different areas of said test sample can be selected for analysis.

4. The combination of claim 3 wherein said light guide means connected to said illumination and collection means comprises flexible fiber optic bundles connected to said opaque means and allowing movement thereof.

5. A glossimeter device for attachment to a spectrophotometer having a polychromatic light source, a light detector and a monochromator for transmitting monochromatic light of different wavelengths, comprising:
 first and second light pipe means for receiving light from said spectrophotometer and transmitting light back to said spectrophotometer;
 connector means operative to detachably connect said first and second light pipe means to said spectrophotometer;
 test sample illumination means connected to said first light pipe means and operative to direct plural light beams onto a surface of said test sample at different angles of incidence;
 light collection means connected to said second light pipe means and operative to collect specular light reflected from said surface at different angles of reflection corresponding to said angles of incidence and providing plural paths of light through said illumination means and said collection means whereby each path includes light directed onto said surface at a predetermined angle and specular light reflected therefrom at a corresponding predetermined angle,
 and a plurality of filters each disposed in a different one of said paths and each being operative to transmit monochromatic light of a different wavelength such that each different angle of incidence corresponds to a different wavelength, whereby said monochromator and said detector are operative to produce an output signal proportional to the intensity of light reflected from said sample in each of said paths.

6. The combination of claim 5 comprising an opaque head encompassing said illumination means and said collection means and having an opening therein adapted to surround an area of said surface being analyzed, said opaque head and said collection means and said illumination means being assembled together and being movable as a unit, allowing different test samples to be positioned for analysis and allowing different areas of each sample to be selected for analysis.

7. The combination of claim 6 wherein each of said first and second light pipe means comprises flexible fiber optic bundles.

8. The combination of claim 5 wherein said spectrophotometer includes a reference light path and said glossimeter device comprises third light pipe means connected to said connector and operative to transmit light along said reference path of said spectrophotometer.

9. The combination of claim 6 comprising a plurality of lenses forming part of said illumination means and operative to direct beams of light along said angles of incidence on the same area of said test sample and said collection means comprises a plurality of lenses each arranged to receive light reflected from such area and concentrate such light into beams upon entrances to said second light pipe means.

10. The combination of claim 6 wherein each path is substantially coplanar with a plane perpendicular to the surface of the test sample and the planes of each such path are angularly spaced from each other.

* * * * *